United States Patent [19]

Uzan et al.

[11] Patent Number: 5,559,002
[45] Date of Patent: Sep. 24, 1996

[54] APPARATUS FOR AUTOMATICALLY CARRYING OUT A MULTI-STAGE IMMUNOASSAY OF AT LEAST ONE BIOLOGICAL SUBSTANCE IN A PLURALITY OF BIOLOGICAL SAMPLES: METHOD USING SAID APPARATUS

[75] Inventors: Michel Uzan, Les Pavillons Sous Bois; Thierry Gicquel, Jouy Le Moutier; Edouard Lenywojt, Saint Leu D'Esserent; Dario Marminio, Louvres, all of France

[73] Assignee: Laboratoires Biotrol, Paris, France

[21] Appl. No.: 179,543

[22] Filed: Jan. 10, 1994

Related U.S. Application Data

[63] Continuation of Ser. No. 721,520, filed as PCT/FR90/00823, Nov. 16, 1990, published as WO91/07662, May 30, 1991, abandoned.

[30] Foreign Application Priority Data

Nov. 17, 1989 [FR] France .................................. 89 15095

[51] Int. Cl.$^6$ ...................... G01N 33/538; G01N 33/553
[52] U.S. Cl. ................ 435/7.9; 422/62; 422/63; 422/64; 422/67; 435/287.2; 435/287.3; 436/43; 436/47; 436/48; 436/49; 436/50; 436/525; 436/526; 436/541; 436/806; 436/808
[58] Field of Search ........................... 435/7.9, 287, 290, 435/291; 422/62–65, 67; 436/525, 526, 806, 808, 43, 47–50, 541

[56] References Cited

U.S. PATENT DOCUMENTS

| 4,774,055 | 9/1988 | Wakatake et al. ............ 422/64 |
| 5,104,808 | 4/1992 | Laska et al. ................. 422/64 |
| 5,147,529 | 9/1992 | Lee et al. ................... 436/47 |

FOREIGN PATENT DOCUMENTS

| 81400519 | 10/1981 | European Pat. Off. . |
| 86108560 | 4/1987 | European Pat. Off. . |
| 87304644 | 12/1987 | European Pat. Off. . |
| 89115593 | 2/1990 | European Pat. Off. . |
| 8008151 | 7/1980 | France . |
| PCT/EP87/00603 | 4/1988 | WIPO . |

*Primary Examiner*—David Saunders
*Assistant Examiner*—Christopher L. Chin
*Attorney, Agent, or Firm*—Antonio R. Durando; Harry M. Weiss

[57] ABSTRACT

Apparatus for carrying out automatically in several successive steps an immunoassay of at least one biological substance in a plurality of biological samples, and the method and the reagents for the use of the said apparatus.

This assay apparatus comprises:

(1) a samples module (A) consisting of a plurality of holders for tubes (Te) containing the said samples, which samples module is connected to a control microprocessor;

(2) a reaction module (C) consisting of:
 a plurality of holders for tubes (Tr) intended to receive successively an aliquot quantity of the said samples and an aliquot quantity of a suitable reagent, and
 a washing device for the tubes;

(3) a reagent module (E) consisting of a plurality of holders for tubes containing the reagent/reagents suitable for the different assays to be carried out, at least one of the said reagents being in the form of magnetic balls;

(4) a means (B) for collection and distribution of the samples in the tubes (Tr) of the said reaction module;

(5) a means (D) for collection and distribution of the reagents in the tubes of the said reaction module;

(6) a suitable means for reading of the reaction effected in the reaction module; and (7) an information system consisting of a computer for controlling the different modules and means (1) to (6), and permitting the carrying out of a succession of analysis cycles.

15 Claims, 5 Drawing Sheets

APPARATUS FOR AUTOMATICALLY CARRYING OUT A MULTI-STAGE IMMUNOASSAY OF AT LEAST ONE BIOLOGICAL SUBSTANCE IN A PLURALITY OF BIOLOGICAL SAMPLES: METHOD USING SAID APPARATUS

This is a continuation of application Ser. No. 07/721,520, filed as PCT/FR90/00823, Nov. 16, 1990, published as WO91/07662, May 30, 1991, now abandoned.

The present invention relates to an apparatus for carrying out automatically in several successive steps an immunoassay of at least one biological substance in a plurality of biological samples and also to the method and to the reagents for the use of the said apparatus.

The invention applies more particularly, but not restrictively, to the simultaneous detection, on one and the same sample, of ligands, antiligands, haptens or any other biological substance which may be present in the biological fluid to be analyzed.

BACKGROUND OF THE INVENTION

The methods for determining the presence or concentration of ligands or biological substances in biological fluids, by immunological means, are at present well known; they are based on the formation of a complex between the substance to be determined and one or more antibodies, it being possible for one of the components of the complex to be labelled especially by an enzyme, in order to permit its detection and/or its quantitative analysis after separation of the complexed labelled antibody or antigen from the uncomplexed labelled antibody or antigen.

The principle of the RIA and ELISA methods is also well known.

The ELISA technique (enzyme-linked immunosorbent assay) in particular is an immunoenzymatic method of very great sensitivity, for assaying of antibodies, for example, which consists in using an immunoadsorbent complex made up in particular of an antigen fixed on a solid support, for taking up the specific antibodies contained in the biological medium to be tested, such as serum, the immune complex thus obtained being detected by an anti-species antibody labelled by an enzyme, after which a substrate specific to the enzyme is added, whose degradation by the enzyme causes a coloured substance to appear; the strength of the colouring is proportional to the quantity of enzyme which reacts and, thus, to the antibody quantity present in the tested biological medium; the strength of the colouring can be assessed by the naked eye or measured by any suitable means, in particular by photometry.

In the above immunological methods using a heterogenous phase, the nature of this solid phase which serves as a support for the immunological reaction is very important since it determines the sensitivity of the measurement.

The supports which have been proposed for the ELISA test are, in particular, polyacrylamide beads activated by glutaraldehyde (AVRAMEAS and TERNYNCK, Immunochemistry, 1969, 6, pages 53–65); particles of cellulose activated by cyanogen bromide, on which antibodies are fixed by covalent bonds (ENGVALL and PERLMANN, Immunochemistry, 1971, 8, 871–874); polystyrene tubes on the surface of which antigens are fixed by simple physical adsorption (ENGVALL and PERLMANN, J. Immun. 1972, 160, 129–136); discs of paper activated by cyanogen bromide and on which an antibody or an antigen is fixed (BRIGHTON et al. Scand. 1974, 29, 166–174). However, the supports most widely used at present are the surfaces made of plastic material which are offered in the form of microplates with 96 flat-bottomed, U-shaped or V-shaped wells, of polystyrene or PVC, or small bars with 8 wells.

Another support, made up of magnetic balls, also called magnetic beads or magnetic particles, has also been described and may permit the automation of the methods used.

Mention may be made in particular of the magnetic balls described in European Patent 38,730 RHONE POULENC SPECIALITES CHIMIQUES, which describes magnetic polymer latexes, the magnetic balls described in European Patent 125,995 ADVANCED MAGNETICS INC., the magnetic balls described in French Patents 2,262,805 and 2,454,098 CORNING GLASS WORKS or the balls described in European Patent Applications SERONO DIAGNOSTICS PARTNERS 105,714, 190,006, 238,353 and 249,357.

The different magnetic balls described in the abovementioned documents can also be applied for the implementation of an immunoassay such as ELISA or RIA.

Both the RIA method and the ELISA method can be used in several ways:

The indirect method is the simplest for assaying antibodies. The antigen is fixed on the microplate (in the presence of albumin in order to block the unoccupied sites). The serum to be assayed is added and the binding of the antibodies is detected by the addition of anti-Ig antibodies suitably labelled, in particular linked to an enzyme and visualized quantitatively by spectrophotometry after addition of the substrate of the enzyme.

A competitive technique can be used for assaying the antigens. As in the preceding technique, it is the antigen which is always fixed on the plates. A mixture of antigen and of small quantities of antibody is added. The greater the number of antibody molecules neutralised by the antigen molecules, the smaller the antibody quantity fixed on the plate.

Sandwich methods can be used for assaying antigens or antibodies. For assaying antigens, the microplates are covered with the antibody, the antigen is added, then the specific antibody labelled in a suitable manner, in particular linked to an enzyme, is applied and visualized by addition of the substrate. However, the technique is applicable only to those antigens which are divalent or have several determinants. For assaying antibodies, the microplates are in contrast covered with the antigen, and the antibody to be assayed and the antigen labelled by an enzyme are added successively.

However, such methods cannot be completely automated since they do not permit an automatic assay of at least one substance in a plurality of samples. Indeed, the implementation of these different methods only permits assays of the same type in series (competitive or sandwich or immunocapture) parameter by parameter, either continuously or discontinuously, at slow speeds.

OBJECTS OF THE INVENTION

Now, it is desirable, in particular in medical analysis laboratories, to provide automatic devices for random-access multi-parametric assays which can be carried out much more quickly and at less cost.

A random-access multi-parametric assay makes it possible, in particular on one biological sample, to carry out the assay of twenty different parameters and to carry out the assay of only two parameters, for example, on the following sample.

The Applicant company has consequently set itself the aim of providing a method and an apparatus for automatic determination and/or assay of at least one substance, in particular ligands, antiligands, haptens or other biological molecules, which method and apparatus satisfy the practical requirements more so than the apparatuses and methods of the prior art, particularly in that they permit a random-access multi-parametric assay for each sample, in a relatively short time (assays carried out at a high speed) and at less cost, in that they permit the use of far fewer reagents, and more particularly "monoreagents", which are simple to use, and in that they allow different types of assay to be carried out, such as competitive, sandwich, immunocapture.

SUMMARY OF THE INVENTION

The present invention relates to a device for washing which can be used in the implementation of an assay method of the immunological type, characterized in that it comprises at least one means for application of a magnetic field to the lower part of test tubes containing the sample to be analyzed and one or more reagents appropriate to the assays to be carried out, at least one of the said reagents being in the form of magnetic balls, and a washing head comprising at least one means for suction of the liquid contained in the said tubes, at least one means for distribution of a washing liquid to the said tubes and, if appropriate, at least one means for distribution of a suitable substrate.

The present invention also relates to an apparatus for automatic immunoassay of at least one substance in a plurality of samples to be analyzed, in several successive steps constituting an analysis cycle, characterized in that it comprises:

(1) a samples module consisting of a plurality of holders for tubes containing the said samples, which samples module is connected to a control microprocessor;

(2) a reaction module consisting of:

a plurality of holders for tubes intended to receive successively an aliquot quantity of the said samples and an aliquot quantity of a suitable reagent, and a washing device according to the invention, that is to say comprising a means for application of a magnetic field to the lower part of the test tubes and a washing head comprising at least one means for suction of the liquid contained in the said tubes, at least one means for distribution of a washing liquid to the said tubes and, if appropriate, at least one means for distributing a suitable substrate, which reaction module is connected to a control microprocessor;

(3) a reagents module consisting of a plurality of holders for tubes containing the reagent/reagents appropriate to the different assays to be carried out, at least one of the said reagents being in the form of magnetic balls;

(4) a means for collection and distribution of the samples in the tubes of the said reaction module;

(5) a means for collection and distribution of the reagents in the tubes of the said reaction module;

(6) a suitable means for reading the reaction effected in the reaction module, and (7) an information system consisting of a computer controlling the different modules and means (1) to (6), and permitting the carrying out of a succession of analysis cycles.

An analysis cycle according to the invention comprises a series of steps constituting at least one immunological incubation, and a series of steps constituting a visualization incubation, in particular an enzymatic incubation; each step corresponds to a number of sequential positions of a tube in the reaction module, the stopping time of a tube in one position being constant.

According to a characteristic of the invention, the washing head of the fixed washing device of the reaction module comprises, as suction and distribution means, a holder equipped with needles for suction and distribution of a suitable solution, which holder is movable along a vertical axis, its displacement being synchronized with the displacement of the test tubes.

According to another characteristic of the invention, each means for application of a magnetic field advantageously consists of a pair of magnets arranged face to face and on both sides of two consecutive test tubes, brought between the said pair of magnets by means of the rotation of the reaction module.

According to an advantageous feature of this characteristic, each pair of magnets is connected to a metallic armature for channeling the magnetic flux lines, so that the application of the magnetic field is limited solely to two consecutive tubes at a time.

According to another characteristic of the apparatus, the washing device comprises four means for application of a magnetic field, preferably four pairs of magnets.

According to another characteristic of the apparatus according to the invention, the reaction, samples and reagents modules each comprise a ring driven in rotation, the said rotations of the different rings being synchronised by means of the information system.

Figure 4:
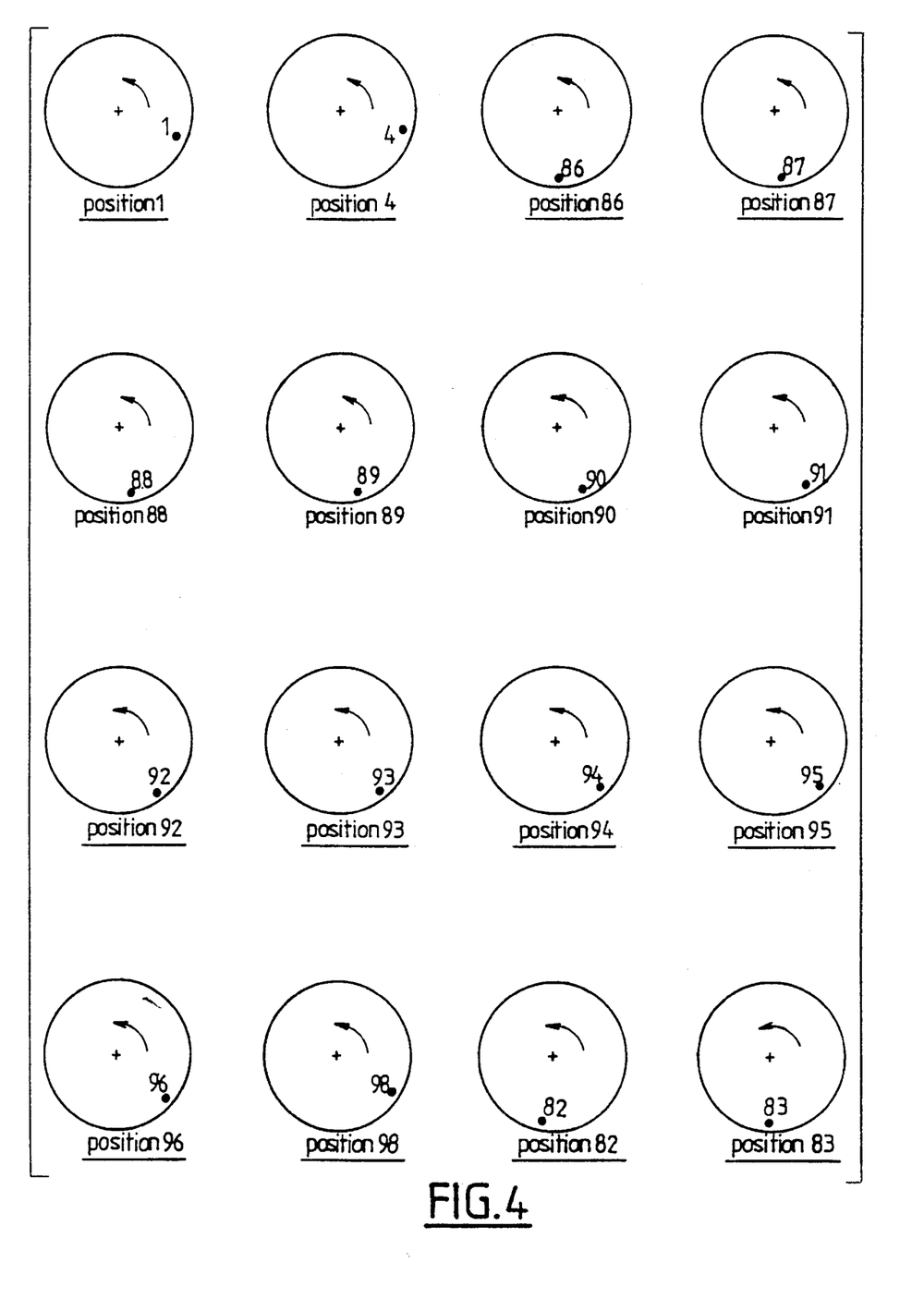
FIG. 4 represents diagrammatically the succession of the steps carried out at the level of reaction module.

According to yet another characteristic of the apparatus according to the invention, the said reaction module comprises a number of positions of tubes corresponding to the execution of at least one analysis cycle comprising the following series of successive steps (with reference to FIG. 4):

deposition of the sample to be analyzed at position 1;

deposition of the suitable reagent at position 4;

premagnetization at position 86;

magnetization and suction at position 87;

washing at position 88;

premagnetization at position 89;

magnetization and suction at position 90;

washing at position 91;

premagnetization at position 92;

magnetization and suction at position 93;

washing at position 94;

premagnetization at position 95;

magnetization and suction at position 96;

possible distribution of the substrate at position 98;

premagnetization at position 82;

reading of the result at position 83.

The washing operation is defined, in the sense of the present invention, as being a set of compulsory steps in the immunological incubation, namely the successive steps of premagnetization of the magnetic balls, magnetization of the said balls, carried out at the same time as the suction of the supernatant and distribution of washing solution.

The washing device according to the invention makes it possible to carry out several washing operations simultaneously on different test tubes.

Some of the steps mentioned above are therefore compulsory, such as the set of steps forming the washing operation; other steps, such as the distribution of a substrate, can prove to be optional, depending on the chosen label.

A complete rotation of the reaction module is defined, in the sense of the present invention, as being the succession of a given number of positions assumed by a tube.

If position 1 is considered as being the starting position for each tube and the number of positions as being, for example, 100, a complete rotation comprises successive positions for a given tube.

All of these successive steps constitute, as defined hereinabove, an analysis cycle comprising, in the case of the distribution of a monoreagent ("monoreagent" assay) two complete rotations of the reaction module, by any suitable means, in particular an electric motor, and in the case of the distribution of two reagents ("twin-reagent" assay) three complete rotations of the reaction module, the reading of the result still being carried out at the end of the final rotation.

According to yet another characteristic of the invention, the stoppage time of a test tube in one position is between approximately 5 and 20 seconds.

It is therefore possible to carry out about 100 analysis sequences per hour.

According to another characteristic of the apparatus according to the invention, the reaction module is additionally connected to a device for regulating the temperature.

According to yet another characteristic of the invention, the apparatus additionally comprises at least one means for decontamination, by flushing, of the means for collection and distribution of the samples and of the reagents.

This decontamination means advantageously consists of a receptacle connected via a pump and a three-way electrovalve, for example, to a reservoir of suitable detergent.

The apparatus according to the invention has the advantage of permitting integral automation of the ELISA, RIA, immunofluorescence techniques, etc., and of permitting, simultaneously on a single sample, the assays of, for example, proteins, haptens and antibodies, in a very short time of less than 1 hour.

The present invention also relates to a method for immunoassay, in particular a competitive or sandwich method, in several successive steps, of at least one substance in a plurality of samples to be analyzed, using as the solid support suitable magnetic balls, which method is characterized in that it comprises for each sample to be analyzed:

*at least one immunological incubation comprising:

the successive distribution of an aliquot quantity of sample, then of an aliquot quantity of suitable reagent, in a test tube driven in rotation at constant speed, at the moment when the latter is in the position suitable for the said distributions, then decontamination of each collection and distribution system, bringing the sample and the suitable reagent into contact for a suitable period of time corresponding to the duration of a complete rotation of a test tube, at least one step involving sedimentation of the magnetic balls, on which may be fixed the substance to be detected, by the application of a suitable magnetic field, at least one step involving washing of the said magnetic balls, and

*a visualisation incubation comprising:

if appropriate, the distribution of a suitable substrate and bringing the latter into contact with the said balls, for a suitable period of time depending on the duration of rotation of the said test tube between the said distribution and the step involving reading of the result, then the reading of the result by any suitable means, the said steps being automated, constituting an analysis cycle such as defined hereinabove and being determined by the synchronous rotations of samples, reagents and reaction modules, bearing respectively the tubes containing the samples to be analyzed, the reagent tubes and the test tubes intended to receive successively the aliquot quantities of the said samples and the aliquot quantities of the suitable reagent/reagents comprising the magnetic balls.

The duration of an immununological incubation in the method according to the invention is equal to a complete rotation of the reaction module; the duration of a visualization incubation is also of the order of one complete rotation of the reaction module and depends on the duration of rotation between the distribution of the substrate and the step involving reading of the result; when the method comprises, for example, two immunological incubations, the reaction module is subjected to three rotations before the reading of the result can be carried out.

According to an advantageous implementation of the method according to the invention, the analysis cycle comprises a single immunological incubation and a visualisation incubation consisting of an enzymatic incubation, which incubations comprise the following steps:

I. immunological incubation:

a—the distribution of an aliguot quantity of sample to be analyzed in a test tube;

b—the distribution of an aliquot quantity of suitable reagent in the said test tube;

c—bringing the sample and the reagent into contact for a suitable period of time, corresponding to the duration of a complete rotation of a test tube;

d—a first sedimentation of the magnetic balls, followed by a suction of the supernatant, then a first washing;

e—a second sedimentation of the magnetic balls, followed by a suction of the supernatant, then a second washing;

f—a third sedimentation of the magnetic balls, followed by a suction of the supernatant, then a third washing;

g—a fourth sedimentation of the magnetic balls, followed by a suction of the supernatant, then II. enzymatic incubation h—a distribution of the substrate and bringing the magnetic balls into contact with the said substrate, for a suitable period of time depending on the duration of rotation of the said test tube between the distribution of the substrate and the step involving reading of the result, followed by a sedimentation of the said magnetic balls;

i—then the reading of the result; each of the said steps corresponding to a number of sequential positions of a test tube.

Such a method is referred to hereinbelow as a "monoreagent method".

According to an advantageous feature of this manner of implementation, the incubation is carried out in the presence of a monoreagent consisting of a pre-mixture of a first reagent $R_1$ comprising magnetic balls covered with a substance $S_1$ binding specifically to the substance to be detected, and a second reagent $R_2$ called "conjugate" consisting of a suitable label coupled to a substance $S_2$, which is identical to or different from $S_1$ and which does not react with $S_1$.

According to an advantageous aspect of this feature, the said monoreagent consists of a pre-mixture of a first reagent $R_1$ comprising magnetic balls covered with a substance $S_1$ chosen from the group comprising the suitable monoclonal antibodies, the F(ab')$_2$ fragments of a suitable monoclonal antibody, the suitable polyclonal antibodies, the said antibodies being directed towards the substance to be assayed, and the suitable antigens, in particular the substance to be assayed or one of its fragments, and a second reagent R$_2$ or "conjugate" consisting of alkaline phosphatase associated with a substance S$_2$ chosen from the group comprising the suitable monoclonal antibodies, the F(ab')$_2$ fragments of a suitable monoclonal antibody, the suitable polyclonal antibodies, the said antibodies being directed towards the substance to be assayed, and the suitable antigens, in particular the substance to be assayed or one of its fragments and the antigen-immunoglobulin complexes.

Such a reagent has the advantage of being stable for 30 days or more and of being particularly well adapted to the automatic assay method according to the invention.

According to another manner of implementation of the method according to the invention, the analysis cycle comprises two immunological incubations and one visualisation incubation consisting of an enzymatic incubation, which cycle comprises the following steps:

I. first immunological incubation:

a—the deposition of an aliquot quantity of sample to be analyzed in a test tube;

b—the deposition of an aliquot quantity of suitable reagent in the said test tube;

c—bringing the sample and the reagent into contact for a suitable period of time corresponding to the duration of a complete rotation of a test tube;

d—a first sedimentation of the magnetic balls, followed by a suction of the supernatant, then a first washing;

e—a second sedimentation of the magnetic balls, followed by a suction of the supernatant, then a second washing;

f—a third sedimentation of the magnetic balls, followed by a suction of the supernatant, then a third washing;

g—a fourth sedimentation of the magnetic balls, followed by a suction of the supernatant, then II. second immunological incubation steps b to g are carried out a second time; then III. enzymatic incubation h—a distribution of the substrate and bringing the magnetic balls into contact with the said substrate, for a suitable period of time depending on the duration of rotation of the said test tube between the distribution of the substrate and the step involving reading of the result, followed by a sedimentation of the magnetic balls;

i—then the reading of the result; each of the said steps corresponding to a number of sequential positions of a test tube.

Such a method is referred to hereinbelow as a "twin-reagent method".

According to an advantageous feature of this manner of implementation, the first immunological incubation is carried out in the presence of a first reagent R$_1$ consisting of magnetic balls covered with a substance S$_1$ binding specifically to the substance to be detected, and the second immunological incubation is carried out in the presence of a second reagent R$_2$ called "conjugate", consisting of a suitable label coupled to a substance S$_2$, which is identical to or different from S$_1$ and which does not react with S$_1$.

According to an advantageous aspect of this feature, the first immunological incubation is carried out in the presence of a first reagent R$_1$, consisting of magnetic balls covered with a substance S$_1$ chosen from the group comprising the suitable monoclonal antibodies, the F(ab')$_2$ fragments of a suitable monoclonal antibody, the suitable polyclonal antibodies, the said antibodies being directed towards the substance to be assayed, and the suitable antigens, in particular the substance to be assayed or one of its fragments, and the second immunological incubation is carried out in the presence of a second reagent R$_2$ or conjugate consisting of alkaline phosphatase associated with a substance S$_2$ chosen from the group comprising the suitable monoclonal antibodies, the F(ab')$_2$ fragments of a suitable monoclonal antibody, the suitable polyclonal antibodies, the said antibodies being directed towards the substance to be assayed, and the suitable antigens, in particular the substance to be assayed or one of its fragments and the antigen-immunoglobulin complexes.

For some of the substances to be assayed, an analysis cycle comprising a single immunological incubation and a visualisation incubation is necessary; these are in particular α-fetoprotein (AFP), LH, FSH, hCG, IgE's and prolactin, and this non-restrictively.

For other substances, the analysis cycle comprises two immunological incubations and a visualisation incubation; these are in particular, and non-restrictively, TSH, T3, total T4 and free T4 and cortisol, or else antibodies appearing during infections, in particular due to a parasite (toxoplasmosis for example), a virus (rubella, IHV, for example) or a microorganism (Chlamydia, for example).

As regards these latter substances (antibodies), the method according to the invention makes it possible to carry out assays while omitting the pre-dilution step which is usually necessary.

According to yet another manner of implementation of the method according to the invention, it additionally comprises a multiparametric calibration step, carried out in particular prior to the assay of the samples.

The method according to the invention has a number of advantages:

it does not necessitate a calibration for each series of assays, one calibration of the different batches of reagents being sufficient;

it also makes it possible to calibrate, in a single step, all the substances which may possibly be assayed;

it moreover permits a multi-parametric assay for one sample, it also makes it possible to achieve a particularly high speed of assay (for example 100 assays in 50 minutes).

The present invention furthermore relates to an immunodiagnostic reagent consisting of magnetic balls covered with a substance binding specifically to the substance to be detected, in suspension in a suitable liquid, characterized in that the said balls consist of an organic matrix enclosing a magnetic charge, the said balls having a magnetisable material mass/non-magnetisable material mass ratio greater than or equal to 45%.

According to a particularly advantageous embodiment of the said reagent, it consists of magnetic balls whose magnetisable material mass/non-magnetisable material mass ratio is between 60 and 70%.

In a particularly advantageous manner, the organic matrix is a latex of polymers, such as polystyrene or divinylbenzene.

The said reagent preferably consists of magnetic balls having a diameter of less than 1.5 μm and more particularly between 0.7 and 1.5 μm.

As examples of magnetic balls having such properties, mention may be made of the particles described in European Patent 38730, in the name of RHONE-POULENC SPECIALITES CHIMIQUES and called "ESTAPOR balls".

In a particularly advantageous manner, the said reagent consists of magnetic balls covered with a substance $S_1$ chosen from the group comprising the suitable monoclonal antibodies, the $F(ab')_2$ fragments of a suitable monoclonal antibody, the suitable polyclonal antibodies, the said antibodies being directed towards the substance to be detected, and the suitable antigens, in particular the substance to be detected or one of its fragments.

The coupling of the said substance on such magnetic particles can be achieved according to the coupling techniques by means of covalent bonds described in the prior art and in particular in accordance with the operating method described by WOOD et al. in the Journal of Clinical Chemistry and Clinical Biochemistry, vol. 21, 1983, pages 789–797.

According to another embodiment of the said reagent, it consists of a pre-mixture comprising the said magnetic balls covered with a substance $S_1$ and a conjugate consisting of a suitable label coupled to a substance $S_2$, which is identical to or different from $S_1$ and which does not react with $S_1$, which pre-mixture is formed for the implementation of the method according to the invention.

According to an advantageous feature of this embodiment, the reagent comprises a conjugate consisting of alkaline phosphatase associated with a substance $S_2$ chosen from the group comprising the suitable monoclonal antibodies, the $F(ab')_2$ fragments of a suitable monoclonal antibody, the suitable polyclonal antibodies, the said antibodies being directed towards the substance to be assayed, and the suitable antigens, in particular the substance to be assayed or one of its fragments and the antigen-immunoglobulin complexes.

The said reagent consists in particular of a solution containing 0.1% W/V of magnetic balls (i.e. 1 g dry weight of magnetic balls in 1 liter of a suitable buffer).

Such a reagent is particularly well suited to the automatic implementation, on an apparatus such as described hereinabove, of the method according to the invention, because, while consisting of a solid phase, it can be manipulated like a liquid, thus permitting a saving in time and a simplicity in the execution of the different operations necessary for the immunoassay techniques and in particular for the ELISA method.

Furthermore, the high magnetic charge of the balls forming the reagent makes possible, under the action of a suitable magnetic field, an extremely short magnetization period, permitting the total separation of the said balls from the supernatant. By way of example, this duration of magnetization is 15 seconds under the action of a magnetic field consisting of two magnets of approximately 1023 tesla, permitting a high speed of execution of the assays on the automatic analyser.

Moreover, the considerable reaction surface of the magnetic balls means that, whatever the substance to be assayed, the duration of an immunological incubation is always equal to a complete rotation of the reaction module.

The present invention furthermore relates to a diagnostic kit or assembly, ready for use, characterized in that it consists of at least one immunodiagnostic reagent according to the invention.

BRIEF DESCRIPTION OF THE DRAWINGS

In addition to the above features, the invention comprises yet other features which will emerge from the following description in which reference is made to the attached drawings, in which.

It should be understood, however, that these drawings and the corresponding descriptions are given solely by way of illustration of the object of the invention and they do not in any way constitute a restriction.

PREFERRED EMBODIMENTS OF THE INVENTION

Figure 1:
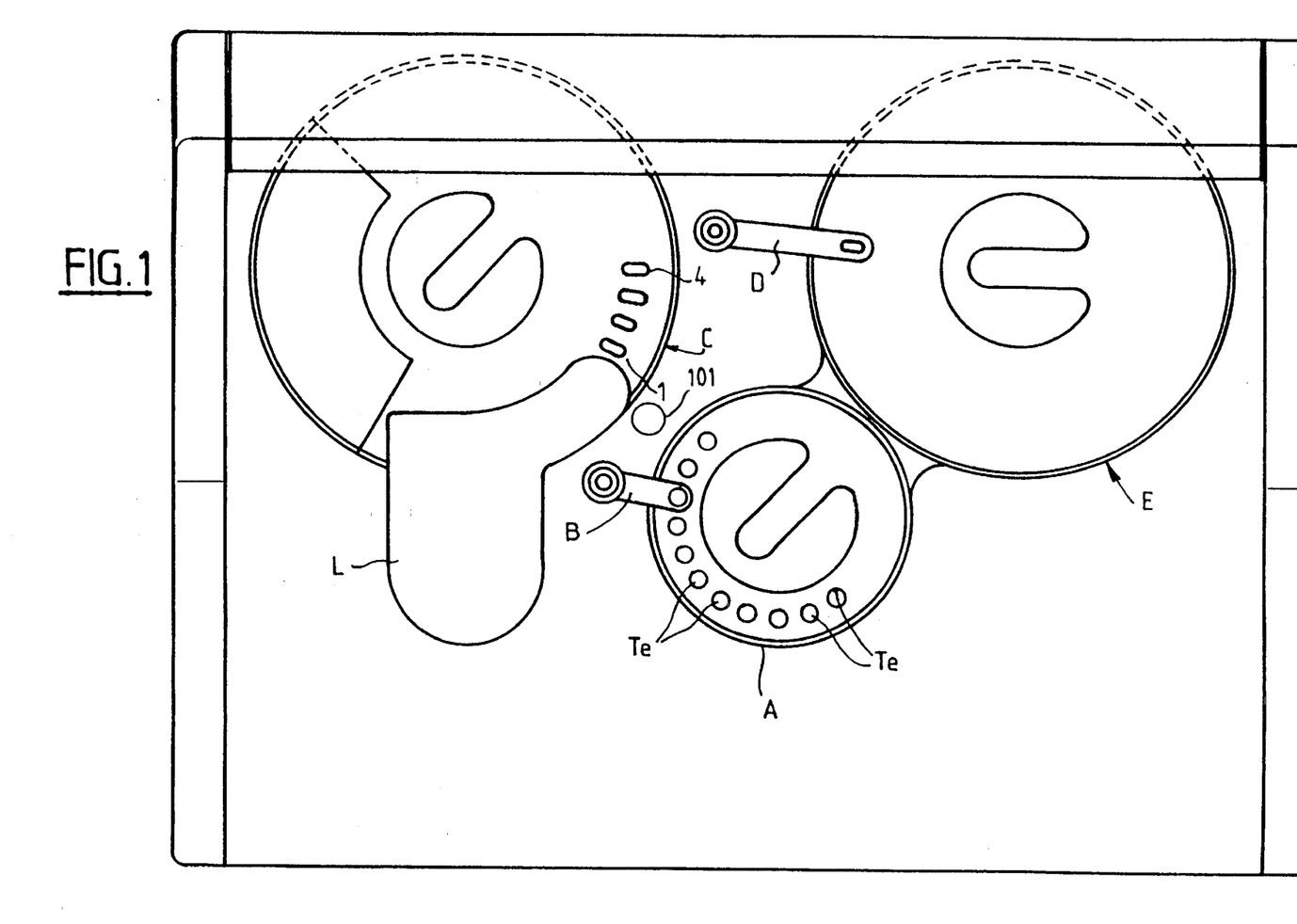
FIG. 1 illustrates diagrammatically the apparatus according to the invention.

The apparatus according to the invention is illustrated diagrammatically in FIG. 1.

It comprises a samples module A, a reaction module C and a reagents module E, each module consisting essentially of a ring equipped with movable holders for test tubes and driven in rotation by an electric motor under the control of a microprocessor. A control unit consisting of a computer provides for the coordination of the functioning, and in particular of the rotations of the three modules A, C and E in such a way that they are synchronized.

The samples module A comprises a holder intended to receive a plurality of tubes Te arranged in a ring and each containing a sample of biological fluid in which at least one substance is to be assayed. The holder can advantageously comprise a second series of positions intended to receive vials containing calibration solutions.

The samples module A is connected to an arm B for collecting and distributing the samples.

The reagents module E supports a plurality of tubes or vials containing the reagents suitable for the various assays to be carried out, and it is connected to an arm D for collecting and distributing the said reagents.

The reaction module C supports a plurality of test tubes and comprises a fixed washing device consisting of a washing head L and at least one means for application of a magnetic field to the lower part of the test tubes.

In a preferred embodiment of the apparatus according to the invention, the washing head L consists of a holder for suction and distribution needles, the said holder resting on a bracket and being movable along a vertical axis.

The needle holder is equipped preferably, but not restrictively, with four suction needles, three needles for distribution of a washing solution, and one needle for distribution of a substrate.

The reaction module C can advantageously be thermostatted at 37° C.

In a preferred embodiment of this apparatus, the samples module A can comprise up to 36 tubes Te, in particular collecting tubes such as are commonly used in medical analysis laboratories, and up to 18 calibration vials. The reagents module E can comprise up to 20 vials which can contain up to 100 ml of reagent, and the reaction module C holds 100 test tubes (four trays of 25 basins) thus able to occupy 100 different angular positions at which they pause for a constant duration, which is advantageously 10 seconds.

The arm B for collecting and distributing the samples consists of a needle holder resting on a bracket, a needle of suitable diameter and a capacitive level detector, which makes it possible, whatever the volume of sample contained in a tube Te, to immerse the end of the needle into the sample at a predetermined and constant level. In a preferred embodiment of the apparatus, the volume of sample which can be collected by the arm B for collection and distribution of the samples is between 10 and 150 μl.

Figure 5:
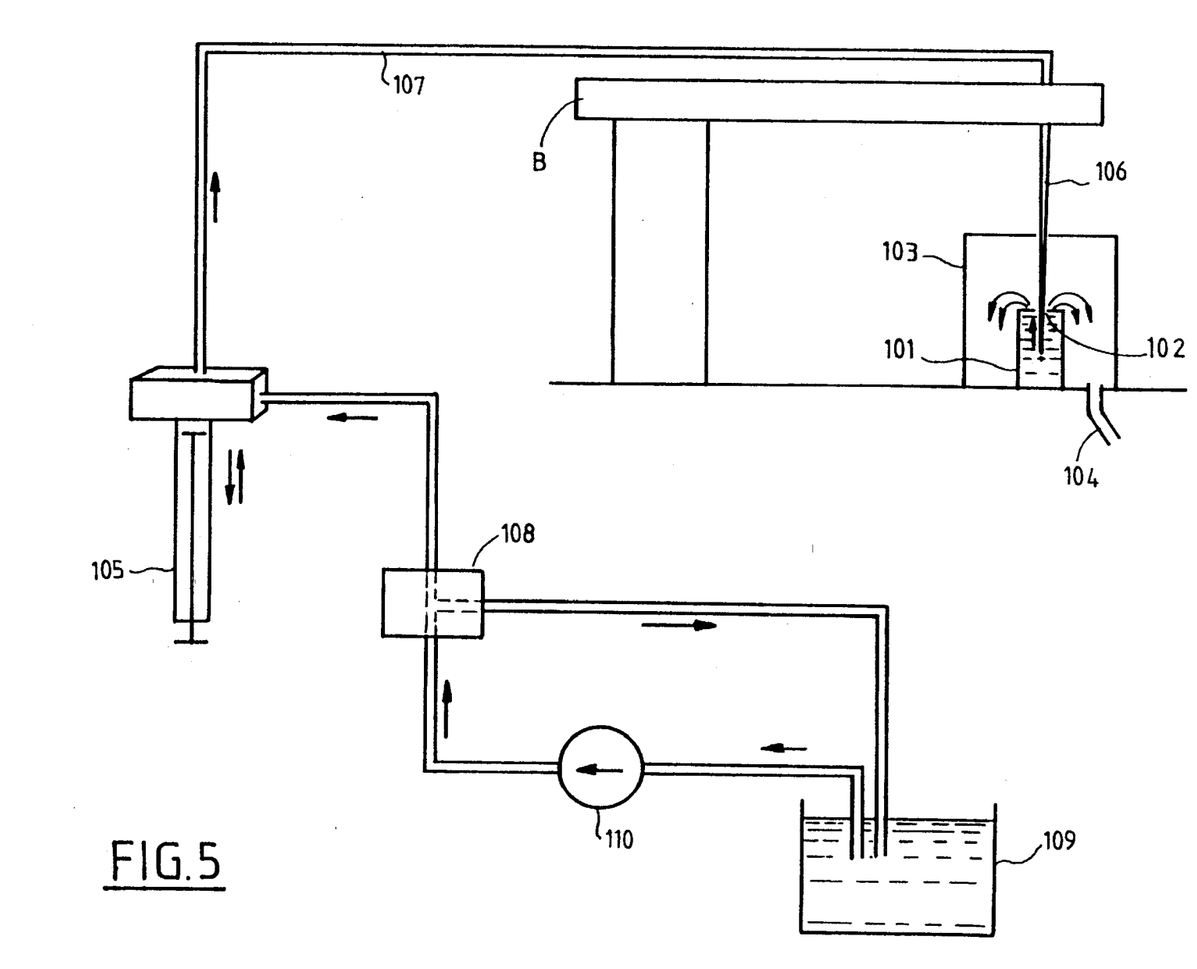
FIG. 5 is a diagrammatic representation of the decontamination device.

The said arm B is advantageously equipped with a decontamination device inside and outside the needle between two collections, comprising (cf. FIG. 5):

a decontamination block 101 comprising an opening 102 in its upper part, containing the decontamination liquid, and included in an enclosure 103 equipped with an emptying means 104, a syringe 105 connected, on the one hand, to the upper part of the needle 106 to be contaminated, via a flexible tube 107 and, on the other hand, to a three-way electrovalve 108 which is itself connected in a loop to a drum of decontamination solution 109 and to a peristaltic pump 110.

After depositing an aliquot quantity of sample in a test tube Tr, the arm B pivots so as to bring the needle to be decontaminated into the decontamination block; when the electrovalve opens, the decontamination solution contained in the decontamination block passes, in the course of 1 second, into the needle to be decontaminated; when the electrovalve c loses, the syringe sucks up a volume, for example 200 μl of decontamination solution, then the electrovalve opens and the syringe simultaneously ejects under pressure 150 μl and retains 50 μl of decontamination solution, which will serve as a volume complement to the next aliquot of sample to be collected, then deposited in a test tube; the needle ejects the decontamination liquid at a pressure sufficient to allow the said liquid to rise in order to wash the needle externally. The liquid is emptied through the opening in the block and the excess is discharged through the emptying means in the enclosure; the electrovalve closes, the arm B is displaced in order to remove the needle from the decontamination block and to bring it above the sample to be collected on the samples module A.

During washing, the syringe acts on the flow rate of decontamination solution and thus promotes the washing.

The arm B collects an aliquot of the said sample and deposits it, together with the volume complement retained in the syringe, in the test tube situated at position 1 of the reaction module C.

The decontamination solution is advantageously a known detergent, for example TWEEN (polyoxyethylene derivatives of sorbitan fatty acid esters).

The three operations, namely collection of the sample, distribution of the sample and decontamination of the needle, are controlled by the microprocessor of the samples module and are performed during the stoppage time of a test tube at position 1 of the reaction module, that is to say advantageously within 10 seconds.

If the following assay relates to the same sample, only the reaction module C is advanced by one tube, the said samples module A remaining stationary. In the opposite case, both the reaction module C and the samples module A are together advanced by one tube. The distribution of the sample at position 1 of the reaction module is repeated for all the samples present on the samples module, and, in respect of a given sample, for all the substances to be assayed in the said sample.

The reagents module E is equipped with an arm D for collection and distribution of the reagents, which arm is essentially analogous to arm B for collection and distribution of the samples and can advantageously be equipped with a comparable decontamination device. In a preferred embodiment of the apparatus according to the invention, the volume of reagent which can be collected and distributed is between 50 and 400 μl.

When the first test tube in which an aliquot of sample has been deposited arrives at position 4 of the reaction module, the arm D for collection of the reagents collects from the level of the reagents module E an aliquot of the appropriate reagent and deposits it in the said test tube at position 4. The reaction module then advances by one position in order to bring the following test tube into position 4. The rotation of the reagents module E, independent of that of the other two modules, is effected as a function of the reagent to be deposited in each of the tubes arriving successively at position 4 of the reaction module C and containing an aliquot of sample to be assayed.

The reagents module E can advantageously comprise means for stirring the reagents, allowing the constituent magnetic balls to be maintained in suspension and thereby guaranteeing their homogeneity. The stirring of the reagents is achieved in particular by means of an alternating rotation of the ring constituting the reagents module, controlled by the microprocessor of the module and taking place for a period of 20 seconds every 10 minutes when the apparatus is on standby, and continuously while the reagents are being collected and distributed.

Figure 2:
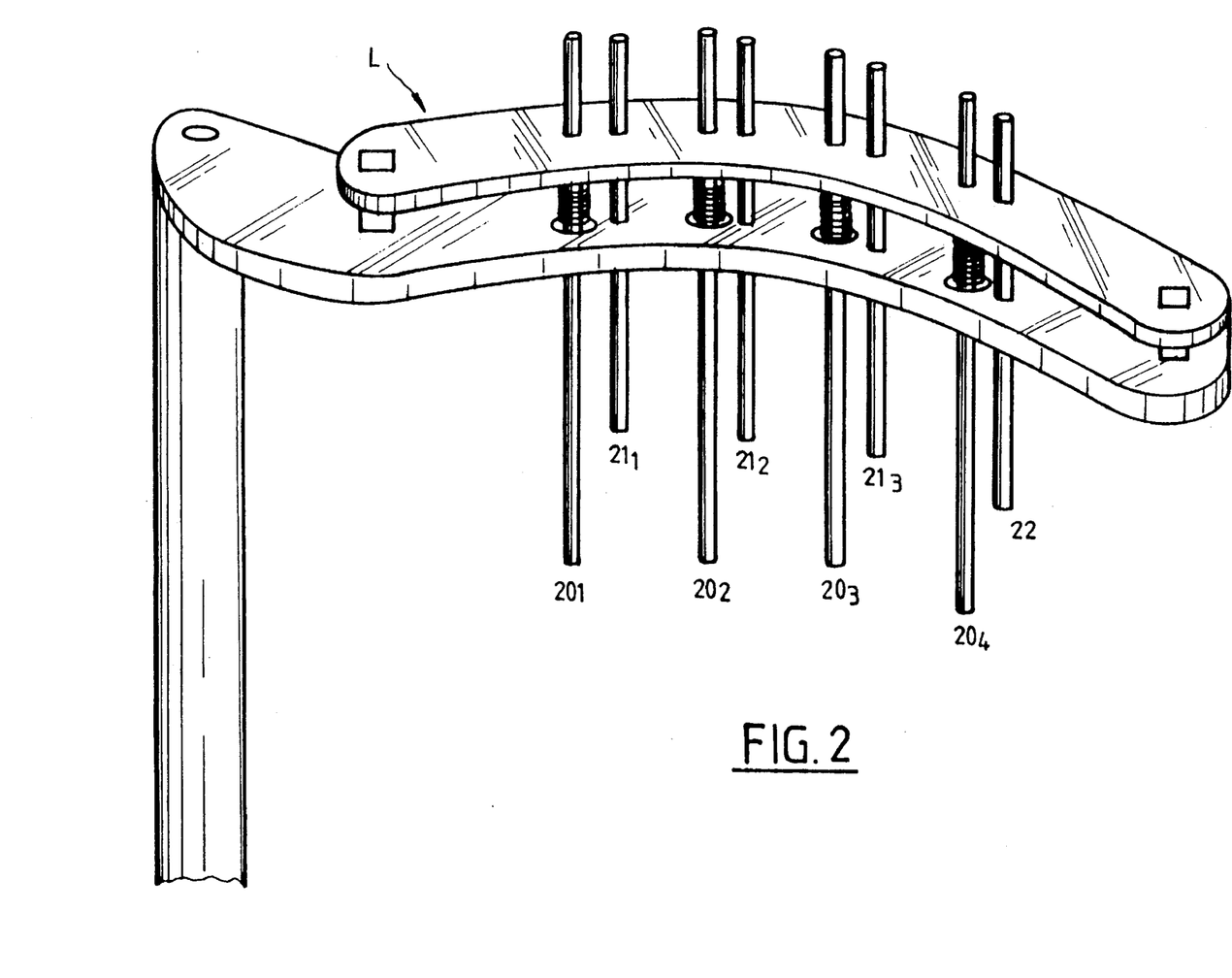
FIG. 2 is a diagrammatic perspective view of the washing head.

FIG. 2 shows a washing head L according to the invention, connected to the reaction module C and comprising a needle holder which advantageously supports 4 suction needles $20_1$–$20_4$, 3 needles $21_1$–$21_3$ for distribution of a washing solution, and one needle 22 for distribution of a substrate, the said needles being arranged in a defined order.

The four suction needles $20_1$–$20_4$ are connected at their upper part by way of a flexible tube to two pumps, which are situated upstream of a collecting bottle.

The three needles for distribution of the washing solution are connected at their upper part by way of a tube to three three-way electrovalves, which are themselves connected on the one hand to a collector and on the other hand to a peristaltic pump, themselves connected to a reservoir containing a washing solution.

The needle for distribution of substrate is connected at its upper part to an electrovalve connected to a bottle of substrate.

The vertical displacement of the needle holder and the synchronization of the functioning of the various means constituting the washing head L are controlled by the microprocessor of the reaction module C.

In a preferred embodiment of the apparatus, the washing device comprises four fixed means for application of a magnetic field to the lower part of the test tubes, the said means each consisting of a pair of permanent magnets 50 (See FIG. 3), each magnet having a magnetic induction of approximately 1023 tesla. The magnets have a dimension corresponding to the surface occupied by two test tubes, thereby making it possible to apply a magnetic field simultaneously to two consecutive tubes.

Figure 3:
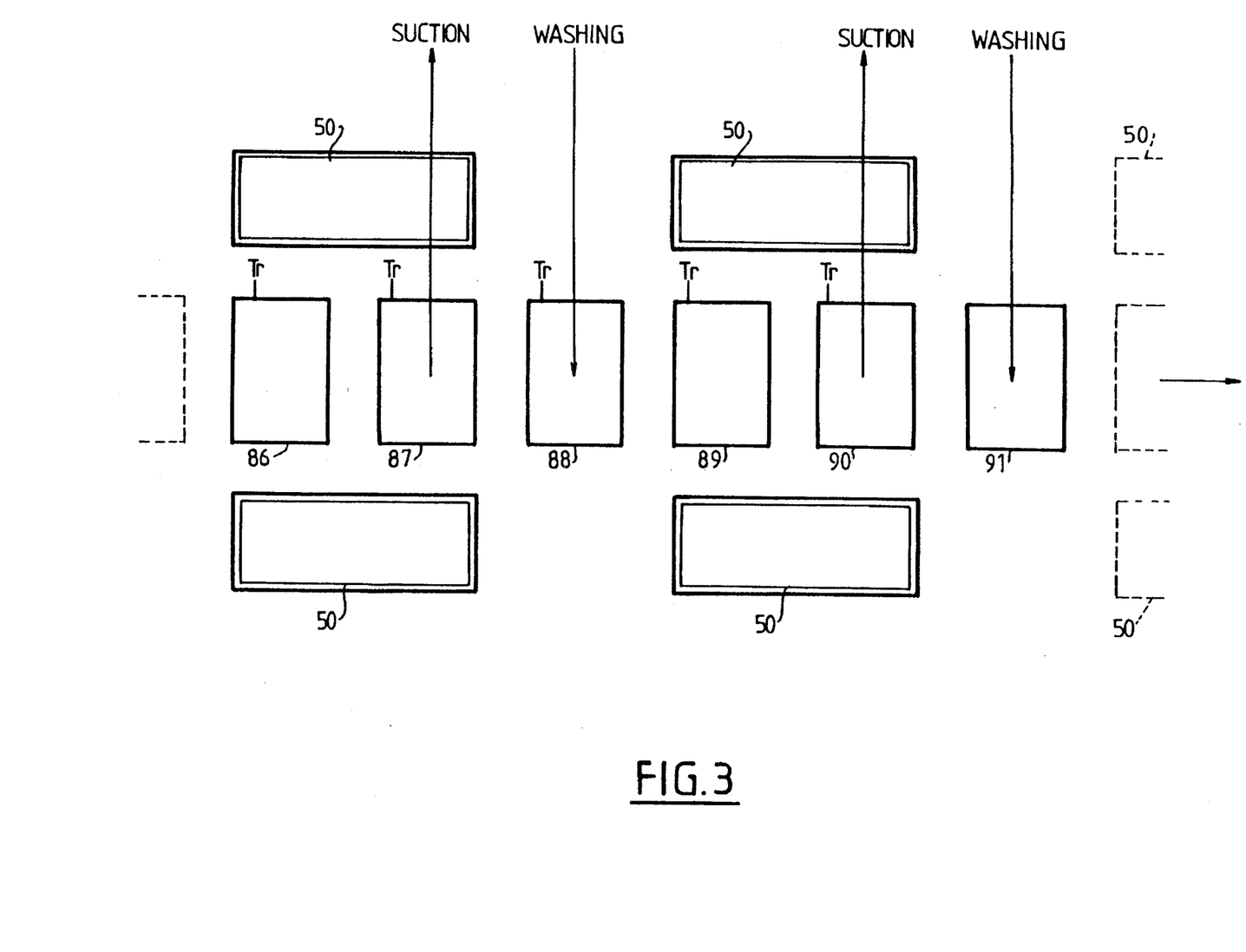
FIG. 3 illustrates diagrammatically the functioning of the washing device.

As can be seen in FIG. 3, the two magnets of one pair are arranged face to face and on both sides of two test tubes. Each pair of magnets is connected to a metal armature for channelling the magnetic flux lines, making it possible to focus the magnetic field solely on the two test tubes brought between the said pair of magnets by means of the rotation of the reaction module, and to remove the upstream test tube and the downstream test tube from the magnetic field.

This FIG. 3 illustrates diagrammatically the functioning of the washing device in a preferred embodiment of the apparatus according to the invention, in which the said device occupies positions 86 to 98 of the reaction module, with the four pairs of magnets situated respectively at positions 86–87, 89–90, 92–93, 95–96; the four suction needles situated respectively at positions 87, 90, 93, 96, the three needles for distribution of the washing solution at positions 88, 91, 94, and the needle for distribution of substrate at position 98 of the reaction module. The duration of magnetization necessary for the sedimentation of the said balls is of the order of 15 seconds.

When a tube is brought into position 86 of the said module, a premagnetization of the magnetic balls is effected at the level of the first pair of magnets and permits their separation from the liquid incubation medium, then at position 87, where the first suction needle is situated, a magnetization of the magnetic balls completes the said separation, and a suction of the liquid contained in the tube is effected; the magnetic balls sedimented at position 87 are washed at position 88 by means of the first washing needle; and the premagnetization, magnetization-suction, washing sequence is again effected at positions 89, 90, 91; 92, 93, 94, then a final sequence comprising the distribution of the substrate instead of washing is effected at positions 95, 96, 98.

Such a washing device allows each tube to be subjected successively to several washing operations, each of which comprises a premagnetization of the magnetic balls, a magnetization associated with a suction of the supernatant, and a distribution of a washing solution, while maintaining a constant speed of rotation of the reaction module.

The reaction module additionally comprises a suitable means for reading the immunological reaction, which reading means can be in particular an interference-filter photometer permitting the systematic reading of each test tube or cell at three different wavelengths. The reading means can advantageously be connected to a means for application of a magnetic field to the lower part of the test tubes which are to be read.

Such an apparatus permits in particular the assay of hCG, TSH, total and free T3, total and free T4, cortisol, IgG's or IgM's present in particular in the following infections: toxoplasmosis, rubella, Chlamydia infections, hepatitis, IHV infections, polypeptides and proteins such as AFP, ACE.

The label can advantageously be alkaline phosphatase.

FIG. 4 shows the sequence of the steps in an analysis cycle as defined hereinabove and comprising an immunological incubation and an enzymatic incubation, in an embodiment of the installation comprising 100 tubes in the reaction module:

at position 1, the deposition of the sample to be analyzed;

at position 4, the deposition of the reagent;

at position 86, the first premagnetization;

at position 87, the first magnetization and suction;

at position 88, the first washing;

the second premagnetization, magnetization, suction and washing series is carried out at positions 89, 90 and 91;

the third premagnetization, magnetization, suction and washing series is carried out at positions 92, 93 and 94;

the fourth series comprises the distribution of the substrate of alkaline phosphatase (PNPP) and comprises premagnetization, magnetization, suction and distribution of the substrate at positions 95, 96 and 98;

the reading of the reaction is preceded by premagnetization at position 82, the reading itself taking place at position 83 by means of a suitable reading system and in particular an interference-filter photometer, with a systematic reading at three different wavelengths, and this in a non-restrictive manner.

This apparatus makes it possible in particular to carry out immunoenzymatic assays as follows:

Example 1: Example of implementation of the immunoassay method using an apparatus according to the invention: assays, in one and the same serum, of hCG, prolactin, anti-Chlamydia IgG's, anti-rubella IgG's, anti-toxoplasmosis IgG's, designated hereinafter "pregnancy plateau".

In this example, the assay of the anti-toxoplasmosis IgG's and IgM's, the anti-rubella IgG's and the anti-Chlamydia IgG's necessitates two immunological incubations, the first in the presence of a first reagent $R_1$ consisting of magnetic balls coupled to a substance $S_1$ binding specifically to the substance to be detected, the second in the presence of a second reagent $R_2$ or "conjugate" and comprising a label coupled to a substance $S_2$, which is identical to or different from $S_1$ but which does not react with $S_1$, while the assay of the hCG and prolactin requires only one immunological incubation, with a premixture of the abovementioned reagents $R_1$ and $R_2$.

The reagents $R_1$ used in this example have been prepared with particles of polystyrene latex of a diameter between 0.7 and 1.5 μl, enclosing a magnetic charge and whose magnetisable material mass/non-magnetisable material mass ratio is between 60 and 70%.

These balls, called "ESTAPOR balls" are supplied by RHONE-POULENC SPECIALITES CHIMIQUES.

The coupling of the substance $S_1$ (monoclonal antibodies, monoclonal antibody fragments F(ab')$_2$, polyclonal antibodies, . . . ) was tried out using the procedure described by WOOD et al. in the Journal of Clinical Chemistry and Clinical Biochemistry, vol. 21, 1983, pages 789–797.

The reagents $R_2$ or conjugates were prepared using a procedure analogous to that described by AVRAMEAS in Immunochemistry, 5, 43, 1969.

The label chosen is alkaline phosphatase (AP). The visualisation substrate is para-nitrophenylphosphate (PNPP).

Table I below shows the composition and concentration of the reagents used.

TABLE I

| Substances to be assayed | Reagent $R_1$ | | Reagent $R_2$ | |
|---|---|---|---|---|
| hCG | ESTAPOR balls-fragment F(ab')$_2$ of an anti-hCG monoclonal antibody | *0.1% W/V solution | AP-fragment F(ab')$_2$ of an anti-hCG monoclonal antibody | **5 mg/l solution |
| Prolactin | ESTAPOR balls-fragment F(ab')$_2$ of an anti-prolactin | *0.1% W/V solution | AP-fragment F(ab')$_2$ of an anti-prolactin monoclonal antibody | **5 mg/l solution |

TABLE I-continued

| Substances to be assayed | Reagent $R_1$ | | Reagent $R_2$ | |
|---|---|---|---|---|
| Toxo G | monoclonal antibody ESTAPOR balls- rubella antigen | *0.1% W/V solution | AP-anti-human-IgG polyclonal antibody | **50 µg/l solution |
| Rubella | ESTAPOR balls- toxoplasmic antigen | *0.1% W/V solution | AP-anti-human-IgG polyclonal antibody | **50 µg/l solution |
| Chlamydia | ESTAPOR balls- Chlamydia antigen | *0.1% W/V solution | AP-anti-human-IgG polyclonal antibody | **50 µg/l solution |
| Toxo M | ESTAPOR balls- fragment F(ab')$_2$ of anti-toxoplasmosis monoclonal antibody | *0.1% W/V solution | Purified toxoplasmic antigen labelled with an animal Ig-AP | **20 mg/l solution |

*solution containing 1 g by dry weight of balls per liter of 0.1 M PBS buffer - pH 7.3 (BSA 5 g/l - NaN$_3$ 1 g/l).
**0.1 M Tris buffer - pH 8 (BSA 5 g/l - MgCl$_2$ 1 g/l - NaN$_3$ 1 g/l).

Table II below shows the quantities necessary expressed in µl of the different products to be distributed, as a function of the substance to be assayed:

TABLE II

| Substance | Serum | Flush | Reagent 1 | Reagent 2 | PNPP |
|---|---|---|---|---|---|
| hCG | 100 | 50 | | 300 | 500 |
| Prolactin | 25 | 50 | | 300 | 500 |
| Toxo G | 10 | 50 | 300 | 400 | 500 |
| Rubella | 10 | 50 | 300 | 300 | 500 |
| Chlamydia | 10 | 50 | 300 | 400 | 500 |
| Toxo M | 10 | 50 | 300 | 400 | 500 |

In this example, the reagents module E comprises:

at position 1, the hCG monoreagent comprising "ESTAPOR" balls covered with a F(ab')$_2$ fragment of a monoclonal antibody directed towards hCG and a conjugate of alkaline phosphatase (AP) with a F(ab')$_2$ fragment of a monoclonal antibody directed towards the hCG, different from the first one;

at position 2, the prolactin monoreagent comprising "ESTAPOR" balls covered with a F(ab')$_2$ fragment of a monoclonal antibody directed towards the prolactin and a conjugate of alkaline phosphatase (AP) with a F(ab')$_2$ fragment of a monoclonal antibody directed towards the prolactin, different from the first one;

at position 3, the reagent $R_1$ for the assay of the anti-toxoplasmosis IgG's comprising "ESTAPOR" balls covered with a toxoplasmic antigen;

at position 4, the reagent $R_4$ for the assay of the anti-toxoplasmosis IgG's, consisting of a conjugate of alkaline phosphatase (AP) with an anti-human-IgG polyclonal antibody;

at position 5, the reagent $R_1$ against rubella comprising magnetic balls covered with a rubella antigen;

at position 6, the reagent $R_2$ against rubella, consisting of a conjugate of alkaline phosphatase (AP) with an anti-human-IgG polyclonal antibody;

at position 7, the anti-Chlamydia reagent $R_1$ comprising magnetic balls covered with a chlamydial antigen;

at position 8, the anti-Chlamydia reagent $R_2$, consisting of a conjugate of alkaline phosphatase (AP) with an anti-human-IgG polyclonal antibody;

at position 9, the reagent $R_1$ for the assay of the anti-toxoplasmosis IgM's, comprising magnetic balls covered with a F(ab')$_2$ fragment of an anti-toxoplasmosis monoclonal antibody;

at position 10, the reagent $R_2$ for the assay of the anti-toxoplasmosis IgM's, consisting of a complex formed by a purified toxoplasmic antigen, labelled with an Ig of animal origin, conjugated with alkaline phosphatase and the samples module A comprises the tube of serum to be analysed.

Six test tubes will therefore receive, in turns, at position 1 of the reaction module C, a suitable quantity of serum and a suitable quantity of "flush" distributed by the arm B for collection and distribution of the samples. Then, when each of the tubes arrives at position 4 on the reaction module C, it receives a suitable quantity:

for tube 1, of hCG monoreagent, for tube 2, of prolactin monoreagent, for tube 3, anti-toxoplasmosis IgG reagent $R_1$, for tube 4, anti-rubella IgG reagent $R_1$, for tube 5, anti-Chlamydia IgG reagent $R_1$, for tube 6, anti-toxoplasmosis IgM reagent $R_1$.

For the assays of hCG and of prolactin requiring only a single immunological incubation, the analysis cycle continues until distribution of the substrate when the tubes arrive at position 98 on the reaction module, which corresponds to a complete rotational turn of the said module. During the following rotational turn, premagnetisation is carried out at position 82 and the reading of each reaction is carried out at position 83 at three different wavelengths (405, 450 and 604 nm).

For the assays requiring two immunological incubations, the first incubation is carried out in the same way as above, except that there is no distribution of substrate at position 98; in fact, when the tubes arrive at position 4 in the second rotational turn of the reaction module C, they receive respectively a suitable quantity:

for tube 3, of anti-toxoplasmosis IgG reagent $R_2$, for tube 4, anti-rubella IgG reagent $R_2$, for tube 5, anti-Chlamydia IgG reagent $R_2$, for tube 6, anti-toxoplasmosis IgM reagent $R_2$, for carrying out a second immunological incubation which continues until distribution of the substrate at position 98 of the second rotational turn of the module, then premagnetisation and reading of the result are carried out respectively at position 82 and 83 on the third rotational turn of the said module.

Table III below shows the analysis cycle for each of the substances:

TABLE III

| POSITION OF THE REACTION MODULE | | hCG (TUBE 1) PROLACTIN (TUBE 2) | TOXO G (TUBE 3) TOXO M (TUBE 4) CHLAMYDIA (TUBE 5) RUBELLA (TUBE 6) |
|---|---|---|---|
| | 1 | Deposition of sample + flush | Deposition of sample + flush |
| | 4 | deposition of mono-reagent ($R_1 + R_2$) | deposition of reagent $R_1$ |
| 1st rotational turn of the reaction module | 86 | Premagnetization | Premagnetization |
| | 87 | Magnetization | Magnetization |
| | 88 | Washing | Washing |
| | 89 | Premagnetization | Premagnetization |
| | 90 | Magnetization | Magnetization |
| | 91 | Washing | Washing |
| | 92 | Premagnetization | Premagnetization |
| | 93 | Magnetization | Magnetization |
| | 94 | Washing | Washing |
| | 95 | Premagnetization | Premagnetization |
| | 96 | Magnetization | Magnetization |
| | 98 | Deposition of substrate | |
| | 4 | | Deposition of reagent $R_2$ |
| 2nd rotational turn of the reaction module | 82 | Premagnetization | |
| | 83 | Reading of result | |
| | 86 | | Premagnetization |
| | 87 | | Magnetization |
| | 88 | | Washing |
| | 89 | | Premagnetization |
| | 90 | | Magnetization |
| | 91 | | Washing |
| | 92 | | Premagnetization |
| | 93 | | Magnetization |
| | 94 | | Washing |
| | 95 | | Premagnetization |
| | 96 | | Magnetization |
| | 98 | | Deposition of substrate |
| 3rd rotational turn of the reaction module | 82 | | Premagnetization |
| | 83 | | Reading of result |
| TIME OF 1st RESULT | | 30 MINUTES | 47 MINUTES |

For a stoppage time of the test tubes of 10 seconds in each position of the reaction module C, the first result is obtained after 30 minutes for the assays requiring only a single immunological incubation and after 47 minutes for the assays requiring two immunological incubations.

Thus, the time necessary for carrying out 100 assays requiring one immunological incubation is approximately 50 minutes and the time necessary for carrying out 100 assays requiring two immunological incubations is approximately 65 minutes.

The example which has just been described concerns the assay of several different substances present in the same sample of serum. It will be understood that it is possible to assay in another sample of serum only one single substance, such as prolactin for example. This is therefore a random-access multi-parametric assay, which permits the detection of a different number of substances in each sample.

It should be noted that the method described hereinabove, implemented in the apparatus according to the invention, has the advantage of comprising incubation steps of the same duration, regardless of the substance to be determined, the concentration of conjugate appropriate to each substance being adjusted in such a way that the incubation steps are effectively of the same duration.

Example 2: assay of 15 different parameters.

Table IV below shows the quantities of the different substances to be added:

| | *SERUM | *FLUSH | Reagent 1 | *Reagent 2 | *SUBSTRATE |
|---|---|---|---|---|---|
| AFP | 20 | 50 | 300 | | 500 |
| LH | 100 | 50 | 300 | | 500 |
| FSH | 100 | 50 | 300 | | 500 |
| hCG | 100 | 50 | 300 | | 500 |
| IgE | 20 | 50 | 300 | | 500 |
| PRL | 25 | 50 | 300 | | 500 |

|           | *SERUM | *FLUSH | Reagent 1 | *Reagent 2 | *SUBSTRATE |
|-----------|--------|--------|-----------|------------|------------|
| CHLAMYDIA | 10     | 50     | 300       | 400        | 500        |
| CORTISOL  | 100    | 50     | 100       | 150        | 500        |
| RUBELLA   | 10     | 50     | 300       | 300        | 500        |
| T3        | 150    | 50     | 200       | 400        | 500        |
| T4        | 100    | 50     | 200       | 400        | 500        |
| T4, free  | 100    | 50     | 150       | 200        | 500        |
| TOXO G    | 10     | 50     | 300       | 400        | 500        |
| TOXO M    | 10     | 50     | 300       | 400        | 500        |
| TSH       | 150    | 50     | 150       | 400        | 500        |

*all the volumes are expressed in μl.

In a general manner, the reagent used for the assay of the substances requiring only one immunological incubation consists of balls covered with a F(ab')$_2$ fragment of a monoclonal antibody directed towards the substance to be assayed and a conjugate of AP with F(ab')$_2$ of a monoclonal antibody different from the first one, directed towards the substance to be assayed.

As regards the substances requiring two immunological incubations:

cortisol: the first reagent consists of balls covered with anti-cortisol polyclonal antibodies and the second reagent consists of cortisol labelled with AP;

total T3, free T3, total T4 and free T4: the first reagent consists of balls covered with anti-T3 or -T4 monoclonal antibodies in F(ab')$_2$ form and the second reagent consists of T3 or T4 labelled with AP;

TSH: the first reagent consists of balls covered with anti-TSH monoclonal antibodies in F(ab')$_2$ form and the second reagent consists of F(ab')$_2$ fragment of another monoclonal antibody directed towards the TSH labelled with AP.

As in Example 1, the assay of a number of different parameters can be programmed for each sample to be analyzed.

Example 3: Role of the magnetisable mass of the reagents in the implementation of the method.

If an assay is carried out, such as described in Example 1 hereinabove, with magnetic balls (DYNAL S.A.) having the following characteristics:

| Diameter:                  | 2.8 μm ± 0.2 μm       |
| Coefficient of variation   | 5% (generally < 2%)   |
| Magnetisable material mass | 12 ± 2%,              | the latter, whose magnetisable material mass is 12%, are suctioned during washing, and consequently no result can be obtained; in contrast, the magnetic balls according to the invention, whose magnetisable material mass is greater than 45%, make it possible to obtain results in very short periods of time.

As emerges from the above, the invention is not in any way limited to those of its modes of implementation, embodiment and application which have just been described in a detailed manner; on the contrary, it encompasses all the variants which may occur to the person skilled in the art, without departing from the framework or the scope of the present invention.

We claim:

1. Device for washing, which can be used in solid phase heterogeneous immunoassays, using a solid support in the form of magnetic balls, said device comprising:

(1) four means for application of a magnetic field to the lower part of test tubes Tr containing the sample to be analyzed and one or more reagents appropriate to the assays to be carried out, one of said reagents consisting of magnetic balls covered with a substance binding specifically to the substance to be detected, in suspension in a suitable liquid, wherein said balls consist of an organic matrix enclosing a magnetic charge, said balls having a magnetizable-material-mass/non-magnetizable-material-mass ratio greater than or equal to 45% and each of said means preferably consisting of a pair of magnets arranged face to face and on both sides of two consecutive test tubes, each pair of magnets being connected to a metallic armature for channelling said magnets' magnetic flux lines and (2) a washing head (L) comprising on a means holder:
  (i) four means for suction of the liquid contained in said test tubes,
  (ii) three means for distribution of a washing liquid to said test tubes and,
  (iii) one means for distribution of an enzyme substrate, said means being arranged on said means holder in the following defined order, from one end to the other end of said means holder: first means of suction, first means of distribution, second means of suction, second means of distribution, third means of suction, third means of distribution, fourth means of suction and means for distribution of a substrate, the first means of suction being necessarily used first when starting the assay, and said washing device being fixed along a horizontal axis.

2. In an automatic analytical apparatus for performing solid phase heterogeneous immunoassays on samples, using a solid support in the form of magnetic balls, the apparatus having:

(1) a sample module A consisting of a plurality of holders for tubes Te which receive said samples;

(2) a reaction module C in which an immunological incubation takes place and consisting of:
  (i) a plurality of holders for test tubes Tr intended to receive successively an aliquot quantity of said samples and an aliquot quantity of a suitable reagent; and
  (ii) a plurality of sequentially located processing positions of said test tubes, for an analysis cycle;

(3) a reagent module E consisting of a plurality of holders for tubes containing the reagent/reagents appropriate to the different assays to be carried out, one of said reagents consisting of said magnetic balls covered with a substance which specifically binds to a substance to be detected, in suspension in a suitable liquid;

(4) means to stepwise position the test tubes Tr in sequence to several processing positions for an analysis cycle;

(5) means for collection and distribution of samples and reagents, respectively from said sample module A to said test tubes Tr and from said reagent module E to said test tubes;

(6) a decontamination means for the decontamination of the means for collection and distribution of the samples and the reagents;

(7) a means for reading an enzymatic reaction effected in each test tube Tr of the reaction module;

wherein the improvement comprises:

the reaction module C, connected to a control microprocessor, includes a washing device of said magnetic balls, consisting of a block fixed along its horizontal axis and comprising:

(i) four means for application of a magnetic field to the lower part of said test tubes Tr containing the sample to be analyzed and one or more reagents appropriate to the assays to be carried out, one of said reagents consisting of magnetic balls covered with a substance which specifically binds to the substance to be detected, in suspension in a suitable liquid, wherein said balls consist of an organic matrix enclosing a magnetic charge, said balls having a magnetizable-material-mass/non-magnetizable-material-mass ratio greater than or equal to 45% and each of said means preferably consisting of a pair of magnets arranged face to face and of both sides of two consecutive test tubes, each pair of magnets being connected to a metallic armature for channelling said magnets' magnetic flux lines, and (ii) a washing head L comprising on a means holder: four means for suction of the liquid contained in said test tubes Tr, three means for distribution of a washing liquid to said test tubes Tr and, one means for distribution of an enzyme substrate, said means being arranged on said means holder in the following defined order, from one end to the other end of said means holder: first means of suction, first means of distribution, second means of suction, second means of distribution, third means of suction, third means of distribution, fourth means of suction and means for distribution of a substrate, the first means of suction being necessarily used first when starting the assay;

wherein means B for collection and distribution of the samples from said sample module A to test tubes Tr of said reaction module and means D for collection and distribution of the reagents from said reagent module E to the tubes of said reaction module are separate means; and wherein all the modules and means are controlled by an information system permitting the carrying out of a succession of analysis cycles, wherein a test tube stays in one processing position (stoppage time) between approximately 5 to 20 seconds, each of the analysis cycles comprising compulsorily, the use of said washing device and allowing the immunological incubation to be of the same duration, regardless of the substance to be determined.

3. Apparatus according to claim 2, wherein the reaction module C is additionally connected to a device for regulating reaction module C's temperature.

4. Apparatus according to claim 2, wherein the washing head L of the washing device of the reaction module comprises, as suction and distribution means, a holder equipped with needles for suction and distribution of wash liquids and enzyme substrates, which holder is movable along a vertical axis, its displacement being synchronized with the means to stepwise position the test tubes Tr, so that each test tube is subjected successively to several washing operations.

5. Apparatus according to claim 2, wherein the decontamination means flushes means B with a decontamination solution to internally and externally wash means B while retaining in means B a small quantity of said decontamination solution, which will serve as a volume complement to the next aliquot of sample to be collected.

6. Apparatus according to claim 2, wherein said reaction, sample and reagent modules each comprises a ring and rotation of the different rings is synchronized by said information system.

7. Apparatus according to claim 6, wherein the located processing positions on the ring of said reaction module C, numbered 1 to 100, correspond to the following series of successive steps:

collection and addition of samples and reagents:
position 1: collection and deposition of the sample to be analyzed with means B for collection and distribution of the samples;
position 4: deposition of the suitable reagent with means D for collection and distribution of the reagents;

immunological incubation:
positions 5–85;

washing operations with said washing device:
1st washing operation:
position 86: premagnetization;
position 87: magnetization and suction;
position 88: washing;
2nd washing operation:
position 89: premagnetization;
position 90: magnetization and suction;
position 91: washing;
3rd washing operation:
position 92: premagnetization;
position 93: magnetization and suction;
position 94: washing;

measurement:
position 95: premagnetization;
position 96: magnetization and suction;
position 98: distribution of enzyme substrate;
position 82: premagnetization;
position 83: reading a result of an enzymatic reaction.

8. Apparatus according to claim 2, wherein after said collection and deposition of the sample to be analyzed at the corresponding processing position with means B for collection and distribution of the samples, said means B is decontaminated inside and outside, between two collections of sample by flushing, including the retaining in said means B of a small quantity of decontamination solution which will serve as a volume complement of the next aliquot of sample to be collected.

9. A method for performing multiple types of heterogeneous immunoassays on at least one sample using a solid support in the form of magnetic balls, in several successive steps, comprising the steps of performing in test tubes, successive collection and addition of samples and of reagents, immunological incubation, washing and measurement of a substance to be detected, said steps being automated, constituting an analysis cycle including a plurality of sequentially located processing positions of said test tubes and being determined by synchronous rotation of samples, reagents and reaction modules, bearing respectively tubes containing samples to be analyzed, reagent tubes and test tubes Tr intended to receive successively aliquot quantities of the samples and aliquot quantities of suitable reagent/ reagents, said reaction module in the form of a ring, having processing positions on said ring, numbered 1 to 100, wherein the improvement consists of:
(a) addition of samples and reagents, always during a first analysis cycle, one of said reagents consisting of magnetic balls covered with a substance which specifically binds to a substance to be detected, in suspension in a suitable liquid, wherein said balls consist of an organic matrix enclosing a magnetic charge, said balls having a magnetizable-material-mass/non-magnetizable-material mass ratio greater than or equal to 45%,
(b) said immunological incubation is of the same duration, regardless of the substance to be detected and is equal to a rotation of the reaction module between processing positions 5 and 85,
(c) washing said magnetic balls of said test tubes Tr with a washing device fixed along a horizontal axis and comprising four means for application of a magnetic field to the lower part of the test tubes Tr containing the sample to be analyzed and one or more reagents, each of said means preferably consisting of a pair of magnets arranged face to face and on both sides of two consecutive test tubes and a washing head L comprising on a means holder: four means for suction of the liquid contained in said test tubes, three means for distribution of a washing liquid to said test tubes and, one means for distribution of an enzyme substrate, said means being arranged on said means holder in the following defined order, from one end to the other end of said means holder: first means of suction, first means of distribution, second means of suction, second means of distribution, third means of suction, third means of distribution, fourth means of suction and means for distribution of the enzyme substrate, the first means of suction being necessarily used first when starting the assay, said washing device being used in each immunological incubation, and
(d) the measurement step comprises the following sequence of processing positions:
position 95: premagnetization;
position 96: magnetization and suction;
position 98: distribution of the enzyme substrate;
position 82: premagnetization;
position 83: reading a result of an enzymatic reaction which is correlated to the presence or absence of the substance to be detected.

10. Method according to claim 9, wherein the analysis cycle comprises a single immunological incubation and as measurement step, a visualization incubation consisting of an enzymatic incubation, which incubations comprise the following steps:
I. immunological incubation and washing:
a—distribution of an aliquot quantity of sample to be analyzed in a test tube with means B for collection and distribution of the samples;
b—distribution of an aliquot quantity of suitable reagent in said test tube;
c—first sedimentation of the magnetic balls, followed by a suction of the obtained supernatant, then a first washing;
d—second sedimentation of the magnetic balls, followed by a suction of the obtained supernatant, then a second washing;
e—third sedimentation of the magnetic balls, followed by a suction of the obtained supernatant, then a third washing;
f—fourth sedimentation of the magnetic balls, followed by a suction of the obtained supernatant, then
II. enzymatic incubation:
g—distribution of enzyme substrate and bringing the magnetic balls into contact with said substrate, for a suitable period of time depending on the duration of rotation of said test tube between the distribution of the substrate and a step of measurement of a coloration, followed by a sedimentation of said magnetic balls; each of said steps corresponding to a number of processing positions of a test tube.

11. Method according to claim 10, wherein the immunological incubation is carried out in the presence of a monoreagent consisting of a pre-mixture of a first reagent $R_1$ comprising magnetic balls covered with a substance $S_1$ which specifically binds to the substance to be detected, and a second reagent $R_2$ consisting of a suitable label coupled to a substance $S_2$, which is identical to or different from $S_1$ and which does not react with $S_1$.

12. Method according to claim 11, wherein the monoreagent consists of a pre-mixture of a first reagent $R_1$ comprising magnetic balls covered with a substance $S_1$ selected from the group consisting of suitable monoclonal antibodies, $F(ab')_2$ fragments of a suitable monoclonal antibody, suitable polyclonal antibodies, said monoclonal or polyclonal antibodies being directed towards a substance to be assayed, and suitable antigens, in particular the substance to be assayed or one of its fragments, and a second reagent $R_2$ consisting of alkaline phosphatase conjugated to a substance $S_2$ selected from the group consisting of suitable monoclonal antibodies, $F(ab')_2$ fragments of a suitable monoclonal antibody, suitable polyclonal antibodies, said monoclonal or polyclonal antibodies being directed towards the substance to be assayed, and suitable antigens, in particular the substance to be assayed or one of its fragments and antigen-immunoglobulin complexes.

13. Method according to claim 9, wherein the analysis cycle comprises two immunological incubations and as measurement step, a visualization incubation consisting of an enzymatic incubation, which incubations comprise the following steps:
I. first immunological incubation:
a—deposition of an aliquot quantity of sample to be analyzed in a test tube with means B for collection and distribution of the samples;
b—deposition of an aliquot quantity of suitable reagent in said test tube;
c—first sedimentation of the magnetic balls, followed by a suction of the obtained supernatant, then a first washing;
d—second sedimentation of the magnetic balls, followed by a suction of the obtained supernatant, then a second washing;
e—third sedimentation of the magnetic balls, followed by a suction of the obtained supernatant, then a third washing;
f—fourth sedimentation of the magnetic balls, followed by a suction of the obtained supernatant, then
II. second immunological incubation:
g—steps c to g are carried out a second time; then
III. enzymatic incubation:
h—distribution of enzyme substrate and bringing the magnetic balls into contact with said substrate, for a suitable period of time depending on the duration of rotation between the distribution of the substrate and a step of measurement of a coloration, followed by a sedimentation of the magnetic balls;

each of said steps corresponding to a number of sequential positions of a test tube.

14. Method according to claim 13, wherein the first immunological incubation is carried out in the presence of a first reagent $R_1$ consisting of magnetic balls covered with a substance $S_1$ binding specifically to the substance to be detected, and the second immunological incubation is carried out in the presence of a second reagent $R_2$, consisting of a suitable label coupled to a substance $S_2$, which is identical to or different from $S_1$ and which does not react with $S_1$.

15. Method according to claim 14, wherein the first immunological incubation is carried out in the presence of a first reagent $R_1$, consisting of magnetic balls covered with a substance S1 selected from the group consisting of suitable monoclonal antibodies, $F(ab')_2$ fragments of a suitable monoclonal antibody, suitable polyclonal antibodies, said monoclonal or polyclonal antibodies being directed towards a substance to be assayed, and suitable antigens, in particular the substance to be assayed or one of its fragments, and the second immunological incubation is carried out in the presence of a second reagent $R_2$ consisting of alkaline phosphatase conjugated to a substance $S_2$ selected from the group consisting of suitable monoclonal antibodies, $F(ab')_2$ fragments of a suitable monoclonal antibody, suitable polyclonal antibodies, said monoclonal or polyclonal antibodies being directed towards the substance to be assayed, and suitable antigens, in particular the substance to be assayed or one of its fragments and antigen-immunoglobulin complexes.

* * * * *